United States Patent [19]

Cain

[11] 4,374,474

[45] Feb. 22, 1983

[54] PRESSURIZED DENSITY MEASURING APPARATUS

[75] Inventor: David E. Cain, Houston, Tex.

[73] Assignee: Halliburton Company, Duncan, Okla.

[21] Appl. No.: 242,024

[22] Filed: Mar. 9, 1981

[51] Int. Cl.³ .............................................. G01N 9/04
[52] U.S. Cl. ..................................... 73/433; 141/326
[58] Field of Search ....................... 73/433, 32 R, 19; 215/260, 220; 220/367; 141/80, 123, 326

[56] References Cited

U.S. PATENT DOCUMENTS

| | | |
|---|---|---|
| 316,048 | 4/1885 | Mayo . |
| 978,265 | 12/1910 | Barnett . |
| 1,229,641 | 6/1917 | Munzer . |
| 1,243,917 | 10/1917 | Bley . |
| 1,712,848 | 5/1929 | Rose . |
| 1,871,075 | 8/1932 | Mott et al. . |
| 2,084,439 | 6/1937 | Hamer . |
| 2,132,736 | 10/1938 | Jones . |
| 2,138,141 | 11/1938 | Cromer et al. ............... 73/19 |
| 2,451,390 | 10/1948 | Humphreys . |
| 2,626,087 | 1/1953 | Howard et al. . |
| 2,667,782 | 2/1954 | Shea . |
| 2,668,437 | 2/1954 | Patch ............................. 73/19 |
| 2,746,284 | 5/1956 | Posey et al. . |
| 3,013,697 | 12/1961 | Gill . |
| 3,129,585 | 4/1964 | Hamilton . |
| 3,271,999 | 9/1966 | Dwyer et al. . |
| 3,747,415 | 7/1973 | Nickles et al. ................ 73/433 |
| 3,898,010 | 8/1975 | Jungbluth et al. . |
| 4,154,543 | 5/1979 | Moewe et al. . |
| 4,164,137 | 8/1979 | Williamson .................... 73/19 |
| 4,197,846 | 4/1980 | Bucalo . |

FOREIGN PATENT DOCUMENTS 226081 12/1924 United Kingdom .

OTHER PUBLICATIONS

Brochure No. SP-11053 published by Halliburton Company, (6-62).
American Petroleum Institute Bulletin, RP 13B: "Standard Procedure for Testing Drilling Fluids", (7th Ed., Apr. 1978), including pp. 3 and 4 thereof, (4-78).
IMCO Drawing No. ESB139008C, (8-76).

Primary Examiner—James J. Gill
Attorney, Agent, or Firm—Lucian Wayne Beavers; James R. Duzan

[57] ABSTRACT

A fluid density measuring apparatus for measuring the density of a fluid in a pressurized state. The apparatus includes a balance arm, a fulcrum for supporting the balance arm, a balance weight slidably disposed on the balance arm, and a pressurizable container disposed on the balance arm for holding a fluid sample. A valve is connected to the pressurizable container for allowing pressurized fluid to flow into the container and for retaining the fluid in the container under pressure. A pump is provided for supplying pressurized fluid to the valve. The pump includes a pump body having a cylindrical bore disposed therein and an outlet port for communicating the bore with the valve. The pump also includes a rotatable piston member, threadedly engaged with the pump body, for pressurizing fluid contained in the bore of the pump body upon rotation of the piston member relative to the pump body. One alternative embodiment is suitable for both pressurized and non-pressurized fluid density measurements. A second alternative embodiment incorporates the pump in a threaded cover for the container, thereby eliminating the valve member.

29 Claims, 17 Drawing Figures

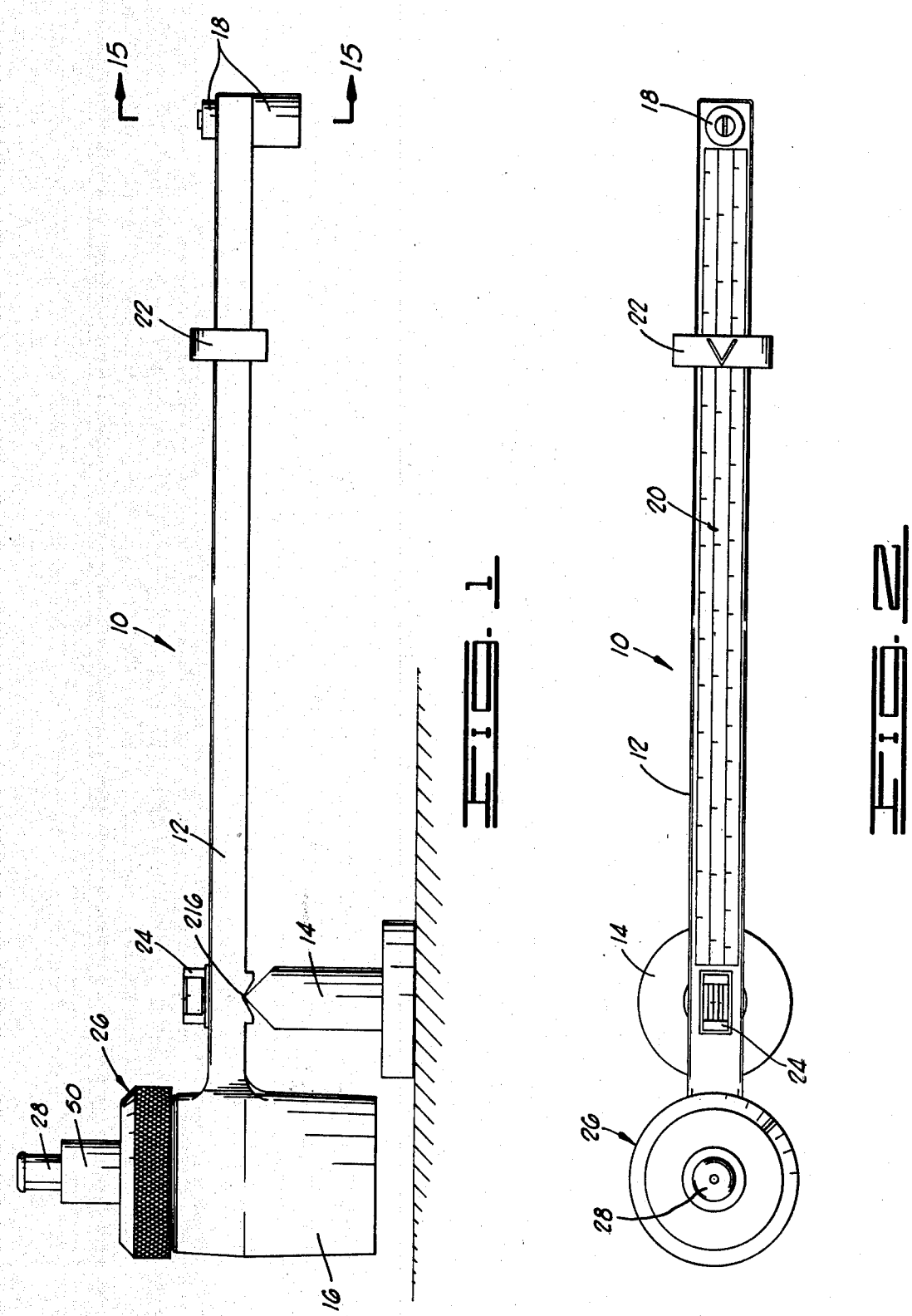

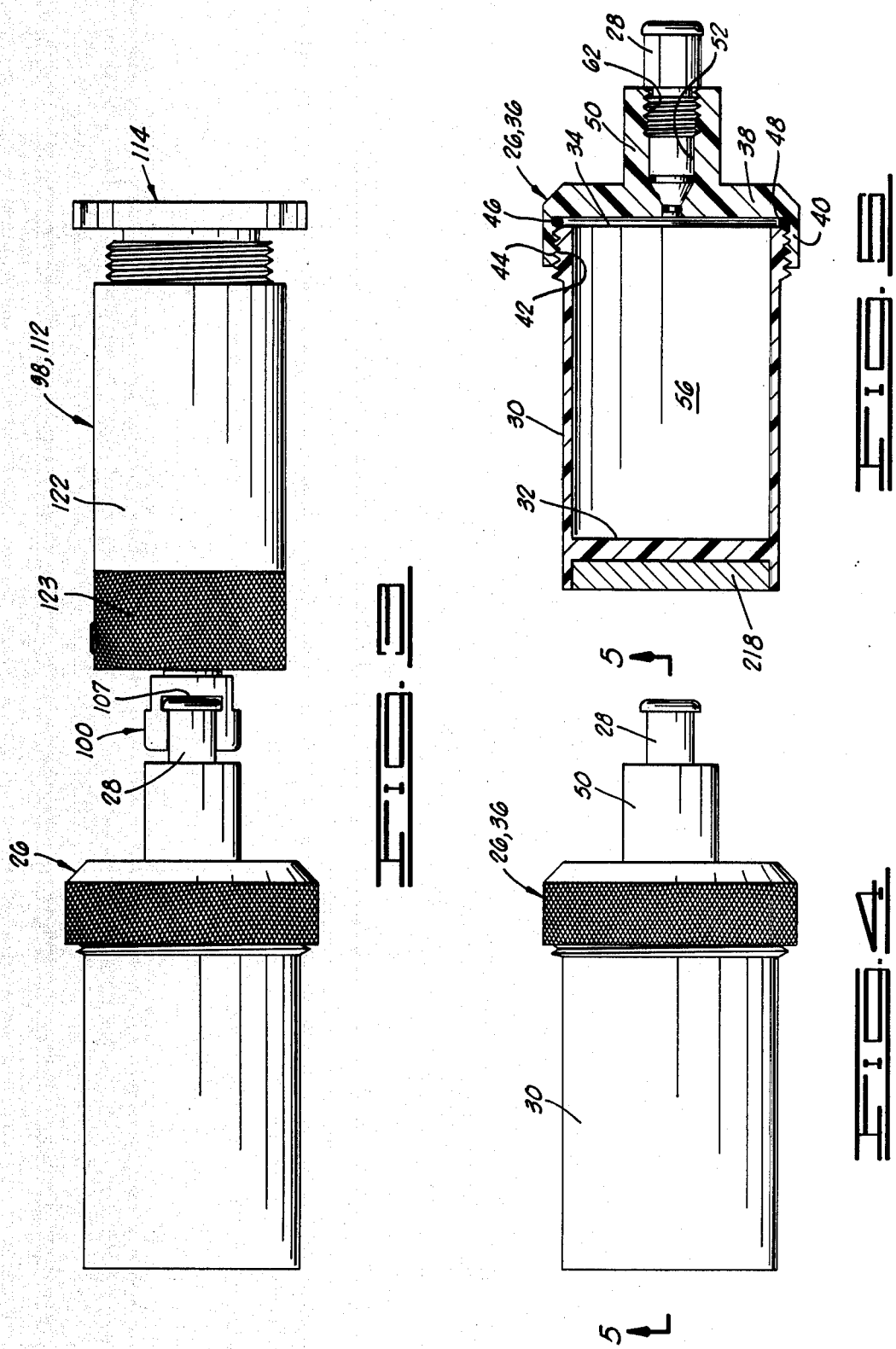

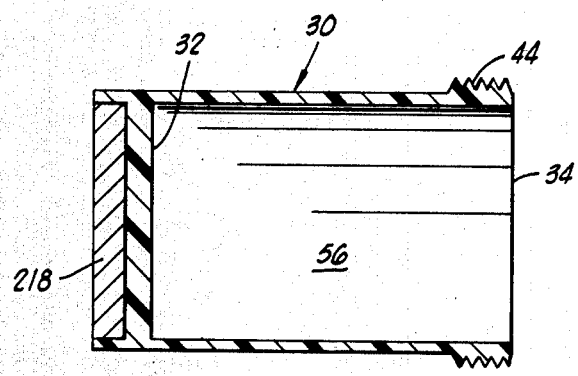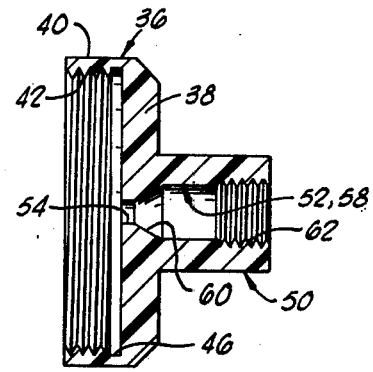
 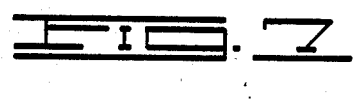
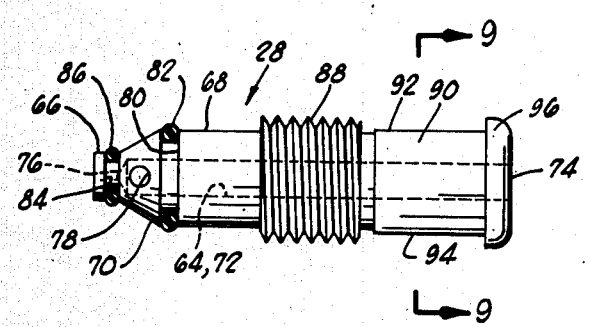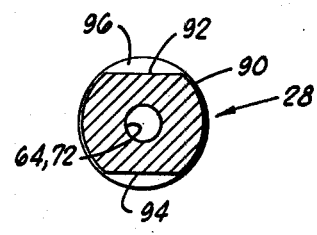
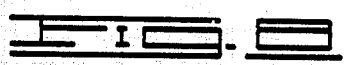 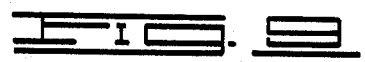
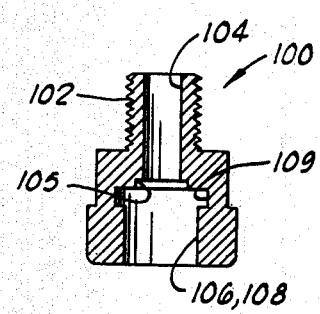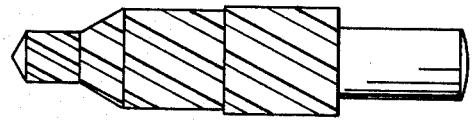
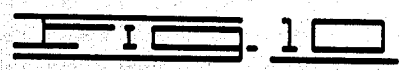 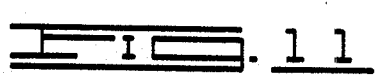

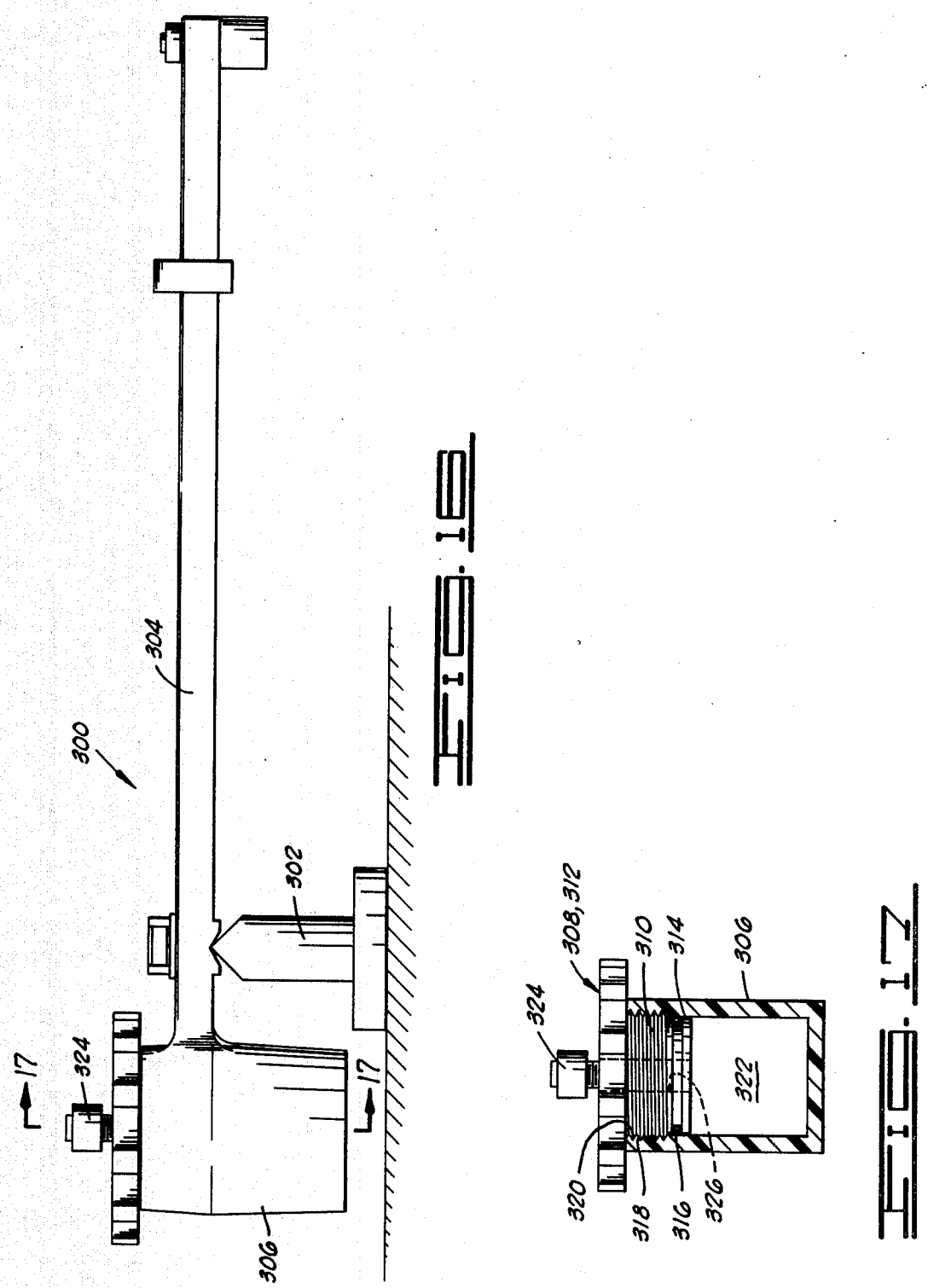

PRESSURIZED DENSITY MEASURING APPARATUS

The present invention relates generally to fluid density measuring apparatus, and more particularly, but not by way of limitation, to such apparatus constructed for use in measuring the density of drilling fluid utilized in the drilling of oil and gas wells.

In the drilling of oil wells drilling fluid, called mud, is used to cool and lubricate the drilling bit and to remove rock fragments cut by the bit. It is very important to know at all times the density of the mud being pumped into the well. For example, if the density is too low and the drill bit hits a high pressure oil and/or gas zone a blowout may quickly develop destroying the drilling rig and injuring or taking the life of personnel working near the rig. On the other hand, if the density is too high and the drill bit hits a low pressure or "thief" zone, thousands of dollars of expensive drilling mud can be quickly lost to the formation.

Various devices are used in determining densities in the oil fields, and the most common of these is referred to as a mud balance. The mud balance includes a base and graduated arm with a cup, lid, knife edge, sliding weight, spirit level, and counterweight. The cup which has a constant volume is attached to one end of the graduated arm and the counterweight is disposed on the opposite end. In operation, the cup is filled with mud and the density of the mud in pounds per gallon is measured by sliding the weight along the graduated arm until the arm is equally balanced on both sides of the knife edge.

A major problem which is associated with the density measurements obtained in the manner just described is that often the fluid being measured contains a considerable amount of entrained air. Thus, the measured density may be in error by the amount of air or gas contained in the sample.

One recent improvement in apparatus and methods for measuring the density of drilling fluids is disclosed in U.S. Pat. No. 3,747,415 to Nickles et al., and assigned to the assignee of the present invention. The Nickles et al. patent discloses a mud balance having a pressurizable container for receiving the mud and including a pump means for applying hydraulic pressure to the mud sample in the container so as to compress any entrained air and thereby largely eliminate the errors in density measurement caused by the entrained air.

A modification of the Nickles et al. device which has the pressurizable container fixedly attached to the balance arm rather than detachably attached to the balance arm has been manufactured and sold by the assignee of the present invention and is included in the prior art. That modified form of the Nickles et al. device is illustrated and described in Brochure No. SP-11053 published by Halliburton Company.

Also, the prior art includes several apparatus for generating hydraulic pressure as a result of rotation of a threaded piston member. One such device is shown in U.S. Pat. No. 978,265 to Barnett. FIG. 3 of Barnett discloses a plunger type hand operated pump which additionally includes a hollow rod "f" disposed about the plunger rod "d". The hollow rod "f" threadedly engages the pump body and may be advanced by rotation to engage the piston "c" so as to provide greater force against the piston "c" than could otherwise be provided by the conventional plunger actuation.

Another group of structures, which utilizes the concept of pressurization of a fluid upon advancement of a threaded member which is rotated, include U.S. Pat. No. 4,154,543 to Moewe et al., U.S. Pat. No. 3,898,010 to Jungbluth et al., and U.S. Pat. No. 2,084,439 to Hamer. All of those devices are directed to a means for disassembly of a tapered connection, such as a tapered connection between a shaft and a member attached to an end of the shaft by a press fit of complementary tapered surfaces. There, the hydraulic pressure is utilized to break the pressed fit connection between the tapered surfaces.

Another somewhat related concept is shown in U.S. Pat. No. 2,451,390 to Humphreys. The Humphreys patent discloses a hydraulic jack which includes a pump, the piston of which is reciprocated upon rotation thereof due to a roller 44 which is received within a continuous cam groove 46.

The present invention provides a fluid density measuring apparatus for measuring the density of the fluid in a pressurized state. The apparatus includes a balance arm, a fulcrum for supporting the balance arm, a balance weight slidably disposed on the balance arm, and a pressurizable container disposed on the balance arm for holding a fluid sample. A valve is connected to the pressurizable container for allowing pressurized fluid to flow into the container and for retaining the fluid in the container under pressure. A pump is provided for supplying pressurized fluid to the valve. The pump includes a pump body having a cylindrical bore disposed therein and an outlet port for communicating the bore with the valve. The pump also includes a rotatable piston member, threadedly engaged with the pump body, for pressurizing fluid contained in the bore of the pump body upon rotation of the piston member relative to the pump body. One alternative embodiment is suitable for both pressurized and non-pressurized fluid density measurements. A second alternative embodiment incorporates the pump in a threaded cover for the container means, thereby eliminating the valve member.

Numerous objects, features and advantages of the present invention will be readily apparent to those skilled in the art upon a reading of the following disclosure when taken in conjunction with the accompanying drawings.

FIG. 1 is a side elevation view of a mud balance including the pressurizable container means and valve of the present invention.

FIG. 2 is a plan view of the structure shown in FIG. 1.

FIG. 3 is a side view of the pressurizable container means, the valve means, the pump means, and the coupler connecting the pump means to the valve.

FIG. 4 is a side view of the pressurizable container means with the valve means in place therein.

FIG. 5 is a sectional view of the apparatus of FIG. 4.

FIG. 6 is a sectional view of the cup of the pressurizable container means of FIG. 5.

FIG. 7 is a sectional view of the cap of the pressurizable container means of FIG. 5.

FIG. 8 is a side view of the valve member.

FIG. 9 is a section view along line 9—9 of the valve member of FIG. 8.

FIG. 10 is a section view of the coupler.

FIG. 11 is a side view of a special drill bit constructed for drilling the valve bore of the cap of FIG. 7.

FIG. 16 is a side elevation view of an alternative embodiment wherein the pump is incorporated in a cover for the container means.

FIG. 17 is a sectional view along line 17—17 of FIG. 16.

Figure 12:
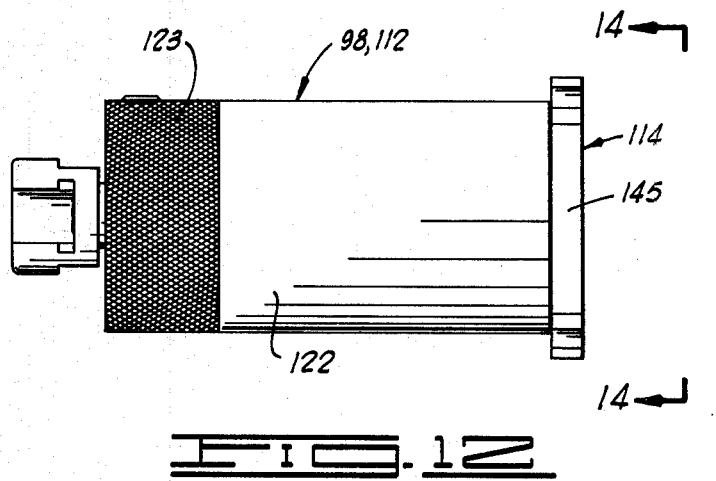
FIG. 12 is a side view of the pump means with the coupler attached thereto.

Referring now to the drawings and particularly to FIGS. 1 and 2, a pressurizable mud balance of the present invention is thereshown and generally designated by the numeral 10. The mud balance 10 may generally be referred to as a fluid density measuring apparatus 10.

The apparatus 10 includes a balance arm 12 and a fulcrum means 14 for supporting the balance arm 12.

Fixedly attached to the left end of balance arm 12, as shown in FIGS. 1 and 2, is an outer cup or non-pressurized first container means 16.

Attached to the right end of the balance arm 12 is a counterbalance weight assembly 18.

Disposed along the upper surface of balance arm 12 are a plurality of scaled indicia 20 as best seen in FIG. 2. A balance weight 22 is slidably disposed upon the balance arm 12. Also mounted on the upper surface of balance arm 12 and directly above fulcrum means 14 is a spirit level 24.

Received within the outer cup 16 is a pressurizable second container means 26 which has a valve member 28 disposed therein. The valve member 28 is connected to the pressurizable second container means 26 for allowing pressurized fluid to flow into container means 26 and for retaining said fluid in said container means under pressure. Valve member 28 is preferably constructed from 7075-T6 aluminum alloy.

The pressurizable container means 26 and the valve member 28 attached thereto may be removed from the outer cup 16 by merely lifting the pressurizable second container means 26 out of cup 16. An external view of the pressurizable container means and valve member 28 is shown in FIG. 4. FIG. 5 shows a view similar to FIG. 4 wherein the pressurizable container means 26 has been sectioned vertically along its longitudinal axis. Referring now to FIGS. 4 and 5 the details of construction of the second container means 26 and the valve member 28 will be further described.

The second container means 26 includes a cup 30 which will be referred to as an inner cup since it is received within the outer cup 16 attached to the balance arm 12.

A sectional view of inner cup 30 alone is shown in FIG. 6, and a sectional view of inner cup 30 attached to the remainder of pressurizable container means 26 and valve member 28 is shown in FIG. 5.

Inner cup 30 has a closed bottom end 32 and an open top end 34.

Pressurizable second container means 26 also includes a cap 36. A sectional view of cap 36 by itself is shown in FIG. 7, and a sectional view of cap 36 attached to cup 30 and valve member 28 is shown in FIG. 5.

Cap 36 includes a disc shaped cover portion 38 which has an annular skirt 40 depending downwardly therefrom. Skirt 40 is internally threaded as shown at 42.

The cap 36 is sealingly connected to the open top end 34 of inner cup 30 by threaded engagement of inner threads 40 with outer threads 44 of inner cup 30.

Skirt 40 of cap 36 also includes an inner annular groove 46 located just above threads 42. An O-ring seal 48 is received within groove 46 and seals against inner cup 30 when cap 36 is connected to cup 30 as is best seen in FIG. 5.

Cap 36 includes a central upwardly extending shoulder portion 50. Centrally disposed through cover portion 38 and shoulder portion 50 of cap 36 is a valve bore generally designated by the numeral 52.

Valve bore 52 includes a smaller diameter bore portion 54 communicated with an interior 56 of inner cup 30. Valve bore 52 also includes a larger diameter bore portion 58 located above smaller diameter bore portion 54. A downwardly tapered annular inner surface portion 60 of bore 52 connects larger and smaller diameter bore portions 58 and 54. An upper part 62 of larger diameter bore portion 58 is internally threaded.

FIG. 11 illustrates a stepped drill bit especially constructed to drill the valve bore 52 in a single operation. The outer profile of the drill bit corresponds to the inner profile of the valve bore 52.

The valve member 28 which is received within valve bore 52 is best shown by itself in FIG. 8, and as assembled with cap 36 in FIG. 5. As seen in FIG. 5, the valve member 28 is threadedly engaged with the internally threaded portion 62 of valve bore 52.

As shown in FIG. 8, the valve member 28 has a fluid passage means 64 disposed therethrough for selectively communicating a source of fluid under pressure with the interior 56 of inner cup 30. The valve member 28 is movable, upon rotation thereof relative to the cap 36 as is further described below, between an open position wherein the fluid passage means 64 is communicated with the interior 56 of cup 30 and a closed position wherein the fluid passage means 64 is isolated from the interior 56 of cup 30.

Valve member 28 includes a smaller outer diameter portion 66 which is closely received within smaller diameter bore portion 54 of cap 36 when valve member 28 is in its said closed position as shown in FIG. 5.

Valve member 28 also includes a larger outer diameter portion 68 which is closely received within larger diameter inner bore portion 58 of valve bore 52 of cap 36.

A downwardly tapered annular outer surface 70 of valve member 28 connects larger and smaller outer diameter portions 68 and 66. The fluid passage means 64 includes an axial passage portion 72 which has an open upper end 74 and a blind lower end 76. Fluid passage means 64 also includes a transverse passage portion 78 which intersects axial passage portion 72 and which is communicated at two diametrically opposed points with tapered annular outer surface 70.

Disposed within larger diameter outer surface portion 68 adjacent a lower end thereof is an annular groove 80 within which is received an upper resilient annular sealing means 82 for sealing between larger outer diameter portion 68 of valve member 28 and larger diameter inner bore portion 58 of valve bore 52 of cap 36.

Smaller diameter portion 66 of valve member 28 has a groove 84 disposed therein adjacent an upper end thereof, within which is received a lower O-ring resilient annular sealing means 86 for sealing between smaller diameter portion 66 of valve member 28 and smaller diameter bore portion 54 of valve bore 52 when valve member 28 is in its said closed position as shown in FIG. 5.

Located above larger diameter portion 68 are external threads 88 for threadedly engaging threads 62 of cap 36. Located above threaded portion 88 of valve member 28 is an upper cylindrical portion 90 having a pair of opposed flats 92 and 94 formed thereon. The flats 92 and 94 are best seen in FIG. 9 which is a section view along line 9—9 of FIG. 8. At an upper end of valve member 28 a flange 96 extends radially outward from cylindrical portion 90. The upper end 74 of axial passage portion 72 of fluid passage means 64 communicates with an upper surface of flange 96.

As mentioned above, FIG. 5 shows the valve member 28 in place within cap 36 and in its closed position. In that closed position the lower seal 86 of valve member 28 engages smaller diameter inner bore portion 54 of cap 36 so as to isolate fluid passage means 64 from the interior 56 of inner cup 30.

By rotating valve member 28 counterclockwise as viewed from above relative to cap 36 the valve member 28 is moved upward relative to cap 36 until the lower seal means 86 moves out of engagement with smaller diameter inner bore portion 54 thereby allowing fluid passage means 64 to communicate with interior 56 of inner cup 32.

The pressurizable container means 26 and valve member 28 are constructed for use with a pump means 98 shown in FIG. 3 for supplying pressurized fluid to the valve member 28 and then to the pressurizable container means 26.

FIG. 3 illustrates the second container means 26 removed from the outer cup 16 and detachably connected to the pump means 98 by a coupler means 100.

Figure 13:
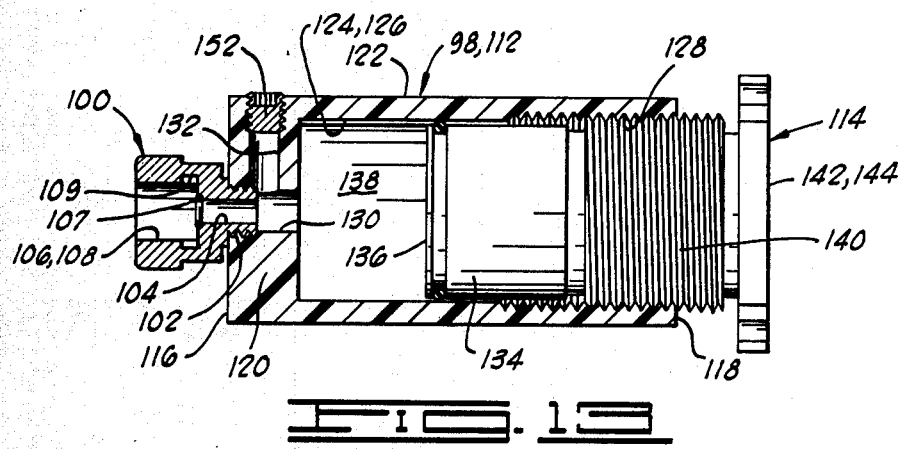
FIG. 13 is a sectional side view of the pump of FIG. 12.

Coupler means 100 is shown in FIGS. 3, 10, 12 and 13 and includes a threaded nipple 102 for attachment to the pump means 98 as best shown in FIG. 13. A fluid passage 104 is disposed through coupler means 100. Disposed within the coupler means 100 is a recess means 106 having a narrow portion 108 for closely receiving the flats 92 and 94 of valve member 98 and having a wider portion 109 for closely receiving the flange 96 of valve member 28.

The valve member 28 is received within the recess 106 upon insertion of flange 96 into wider portion 109 of recess means 106 in a direction parallel to a plane of the flange 96 so that the pump means 98 is communicated with the fluid passage means 64 of valve member 28 when flange 96 is received within the wider portion 109 of recess 106 of coupler means 100.

Located just above wider portion 109 of recess 106 at the lower end of fluid passage 104 is an annular recess 105 (see FIG. 10) within which is received an annular resilient O-ring seal 107 seen in FIGS. 3 and 13. The seal 107 is disposed and seals about the upper end 74 of fluid passage means 64 of valve member 28 when the flange 96 is received within the recess 106.

Referring now to FIGS. 3, 12, 13 and 14 the pump means of the present invention is shown and generally designated by the numeral 98.

The pump 98 includes a pump body generally designated by the numeral 112 and a piston member generally designated by the numeral 114, the details of construction of each of which are best seen in FIG. 13.

The pump body 112 is a hollow cylindrical pump body integrally constructed from a single piece of plastic material.

The pump body 112 includes a closed first end 116 and an open second end 118. First end 116 is closed by a wall 120.

A constant diameter outer cylindrical pump body surface 122 extends from first end 116 to second end 118. Outer cylindrical surface 122 includes a knurled outer surface portion 123 arranged to be gripped by a thumb and forefinger of a human hand.

A bore 124 is centrally disposed in pump body 112 and includes a first bore portion 126 adjacent first end 116 and a threaded second bore portion 128 adjacent second end 118. First and second bore portions 126 and 128 are of substantially equal length.

End wall 120 has an outlet port 130 disposed axially through a center thereof. A monitoring port 132 is disposed radially in said end wall 120 and intersects outlet port 130. Both the outlet port 130 and the monitoring port 132 may be described as being disposed through pump body 112 and communicating with the first bore portion 126 of bore 124.

The piston member 114 is integrally constructed from a second single piece of plastic material and it is preferably machined from a length of solid round barstock. This use of plastic materials allows the pump to be lightweight and corrosion resistant. This second feature is particularly important due to the corrosive environment present in the oil field, especially offshore.

Piston member 114 includes a first outer cylindrical surface 134 adjacent a first end 136 of piston member 114. Surface 134 is closely received within first bore portion 126 of pump body 112 to define a closed pressurizing chamber 138. Pressurizing chamber 138 is defined by first bore portion 126, end wall 120 of first end 116, and first end 136 of piston member 114.

Piston member 114 further includes a threaded second outer cylindrical surface 140 threadedly engaged with threaded second bore portion 128 of bore 124 of pump body 112, so that rotation of piston member 114 relative to pump body 112 moves piston member 114 axially within bore 124 of pump body 112 to vary a volume of pressurizing chamber 138 and thereby vary a pressure exerted upon a fluid contained within pressurizing chamber 138.

Figures 14, 15:
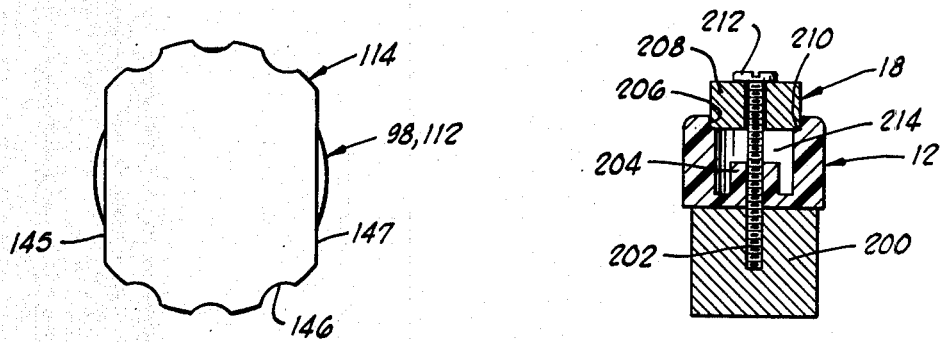
FIG. 14 is an end view of the handgrip of the pump of FIG. 12, taken along line 14—14 of FIG. 12.
FIG. 15 is a sectional elevation view along line 15—15 of FIG. 1 showing the counterbalance weight assembly and the manner in which it is attached to the balance arm.

Located at a second end 142 of piston member 114 is a handgrip means 144. The handgrip means 144 is substantially disc shaped, as is best seen in FIG. 14, and has an outer diameter greater than the constant diameter of outer cylindrical surface 122 of pump body 112. The disc shape of handgrip 144 is interrupted by two chordwise flats 145 and 147 which are for the purpose of allowing pump 98 to fit in a carrying case (not shown). A series of indentations 146 are machined in the outer circumference of handgrip 144 so that handgrip 144 may be more securely gripped by the fingers of a human hand.

As shown in FIG. 12, handgrip means 144 has an inwardmost position wherein handgrip means 144 abuts open second end 118 of pump body 112.

First cylindrical surface 134 of piston member 114 has an annular groove 148 disposed therein adjacent first end 136 of piston member 114. A resilient O-ring seal means 150 is disposed in groove 148 for sealing between first outer cylindrical surface 134 of piston member 114 and first bore portion 126 of pump body 112.

Monitoring port 32 is blocked by a plug 152. Plug 152 may be removed and replaced by a pressure gauge (not shown) for monitoring the pressure of fluid contained in pressurizing chamber 138.

The nipple 102 of coupler 100 is attached to outlet port 130 as previously mentioned.

The construction just described provides a hand operated pump which may be easily operated by holding the pump body 112 in one hand with a thumb and forefinger of that first hand encircling the knurled surface portion 123, and by holding the handgrip 144 in the other hand. Then by rotation of the piston member 114 relative to the pump body 112 fluid contained within pressurizing chamber 138 is pressurized. Thus, in any application like that of the present invention where a small volume of pressurized fluid is required in a generally non-steady state flow, the pump 98 is very suitable.

FIG. 15 is a sectional view along line 15—15 of FIG. 1 which illustrates the details of construction of the counterbalance assembly 18 and its manner of attachment to the balance arm 12.

The counterbalance assembly 18 includes a cylindrical weight 200 which has a threaded bore tapped into an upper surface thereof within which is threadedly received a machine screw 202. An intermediate portion of machine screw 202 threadedly engages an internally threaded annular shoulder portion 204 of balance arm 12.

Balance arm 12 includes a circular opening 206 within which a smaller cylindrical weight 208 of assembly 18 is received and sets against an upward facing shoulder 210. The machine screw 202 loosely fits through a central bore disposed through smaller weight 208 and has a machine screw head 212 which engages an upper surface of smaller weight 208.

An open wall 214 within balance arm 12 which is covered by smaller weight 208 may be partially filled with lead shot or the like (not shown) to provide a fine adjustment of the counterbalance weight.

The pressurizable mud balance 10 of FIG. 1 is utilized with the pump means 98 in the following manner to conduct a measurement of the density of a fluid.

The pressurizable container means 26 is removed from the outer cup 16, and the cap 36 is disconnected from the inner cup 30. The inner cup 30 is then filled with the fluid the density of which is to be measured. The cap 36 is then connected to the cup 30 in the manner shown in FIG. 5. Next the valve member 28 is moved to an open position so that fluid passage means 64 is communicated with the fluid sample contained in the interior 56 of inner cup 30.

Then the bore 124 of pump means 98 is filled with fluid identical to the fluid sample contained in the interior 56 of inner cup 30. This is done by removing the piston member 114 to fill the inner bore and then replacing the piston member 114.

Next, the valve member 28 is connected to pump means 98 by means of coupler means 100. Then the fluid contained within the pump means 98 is pressurized by rotation of the piston member 114 relative to the pump body 112. This pressurized fluid is communicated with the fluid sample contained in the interior 56 of inner cup 30 through the coupler means 100 and valve member 128.

A relatively modest force exerted upon the pump 98 is sufficient to provide fluid pressures within the pump 98 and the container 26 substantially in excess of 100 psig. This pressure exerted upon the fluid sample in cup 30 compresses any entrained air or gas contained in the fluid sample and a small additional volume of fluid is pumped into the interior 56 of inner cup 30 to fill the space created by the compression of the entrained air and gas.

Then with the pump 98 still connected to valve member 28, the valve member 28 is rotated relative to cap 36 to the closed position of valve member 28 as shown in FIG. 5. Thus, the pressurized sample within inner cup 30 is sealed and maintained in its pressurized state by the closing of valve member 28. Then the pump means 98 may be disconnected from valve member 28 and the inner cup 30 may be placed within the outer cup 16 as shown in FIG. 1. Then by sliding the balance weight 22 to a point at which the balance arm 12 is horizontally positioned as indicated by the spirit level 24, the density of the fluid sample contained with inner cup 30 is indicated by the indicia means 20 adjacent the pointer of sliding balance 22.

I have determined that it is very important that the center of gravity of outer cup 16, pressurizable container means 26, valve member 28 and the fluid sample contained within inner cup 30 be below a certain level in order for the mud balance to operate in a stable manner. If that center of gravity is above a horizontal line through a point 216 of the fulcrum means 14 upon which balance arm 12 rests, the mud balance will be unstable and will never balance but rather will tilt completely to the right or to the left.

I have therefore provided a weight means 218 disposed in the bottom end of inner cup 30 as is shown in FIG. 5 for lowering said center of gravity below said horizontal line through the point 216.

The apparatus described above has been discussed only with regard to pressurized density measurement. If it is desired to construct the apparatus only for the conducting of pressurized fluid density measurements, then the pressurizable container 26 may be disposed upon the balance arm 12 in any suitable manner and it is not necessarily disposed within an outer cup such as 16. Indeed, the pressurizable container means 26 could be fixedly attached to the balance arm 12 and still embody many of the concepts of the present invention.

By properly sizing the various components of the apparatus described above, however, it may be satisfactorily used for both pressurized and non-pressurized fluid density measurements. This may be done by using the outer cup 16 to contain the fluid sample when it is desired to conduct a non-pressurized density measurement and by using the pressurizable inner cup 30 to contain the fluid sample when it is desired to conduct a pressurized fluid density measurement.

In a preferred embodiment of such a dual purpose density measuring apparatus, the outer cup 16 has a fixed volume which is equal to a fixed volume of the inner cup 30.

Then the only alteration which need be made to the mud balance as its function is shifted from pressurized to non-pressurized measurements, is that the counter balance weight assembly 18 would include a smaller counter balance weight to be substituted for the larger weight 200 when the apparatus was being utilized to perform a non-pressurized density measurement. This is because in a non-pressurized density measurement the weight of the pressurizable container 26 and valve member 28 would be eliminated and thus a corresponding weight must be eliminated from counter balance weight means 18 which would of course be less than the weight eliminated by the container means and the valve member according to their respective distances from the pivot point 216.

This construction allows the same sliding weight 22 and scale indicia 20 to be utilized regardless of whether a pressurized or a non-pressurized fluid density measurement is being made.

When conducting a non-pressurized fluid density measurement a covering cap (not shown) would be utilized to cover the open end of outer cup 16 in a manner known to those skilled in the art.

It would be possible to have both pressurized and non-pressurized containers with unequal volumes, but in that case the sliding weight 22 would also have to be changed for each test.

Referring now to FIGS. 16 and 17, an alternative embodiment of the fluid density measuring apparatus of the present invention is shown and generally designated by the numeral 300.

Apparatus 300 includes a fulcrum 302, balance arm 304 and container means 306.

A cover means 308 includes a piston member 310 and a handgrip 312. Piston member 310 includes a first outer surface portion 314 closely received within container 306 with an O-ring seal 316 therebetween.

A threaded portion 318 of piston member 310 engages threads 320 of container 306.

Container means 306 and piston member 310 define a closed pressurizing chamber 322. Piston member 310 is longitudinally movable upon rotation thereof to an inwardmost position relative to container means 306 as shown in FIG. 17, at which inwardmost position the pressurizing chamber 322 has a fixed volume.

A pressure regulating means indicated schematically at 324 is connected to a passage 326 through cover 308 which communicates pressure regulator 324 with chamber 322. Pressure regulating means 324 relieves fluid pressure in chamber 322 in excess of a predetermined pressure, e.g. 100 psig.

Thus the embodiment of FIGS. 16 and 17 is operated in the following manner. Cover 308 is removed from container 306. Container 306 is filled with an excessive amount of the fluid to be tested. Then cover 308 is threaded into container 306 until hand grip 312 engages the upper end of container 306 as shown in FIG. 17. The piston member 310 pressurizes the fluid in container 306. When the pressure exceeds the predetermined pressure fluid is vented by pressure regulator 324 to maintain the desired pressure within container 306. Then the balance arm 304 is balanced in a conventional manner and the density of the fluid is indicated by the scale indicia on balance arm 304.

The improvement in accuracy of fluid density measurement provided by a pressurized density measurement utilizing an applied pressure of at least 100 psig is of course dependent upon the amount of entrained air and gas present in the sample. If there is no entrained air or gas then no improvement is provided since even a non-pressurized fluid density measurement would be accurate. The greater the amount of entrained gas present in the fluid sample, the greater the improvement in accuracy is that is provided by the utilization of a pressurized system as disclosed herein. This relationship is shown by the following Table I.

TABLE I

| INITIAL GAS % BY VOLUME | % ERROR (NON-PRESSURIZED) | FINAL GAS % BY VOLUME | % ERROR (PRESSURIZED) |
|---|---|---|---|
| 25 | 25 | 3.75 | 3.75 |
| 20 | 20 | 3 | 3 |
| 15 | 15 | 2.25 | 2.25 |
| 10 | 10 | 1.5 | 1.5 |
| 5 | 5 | .75 | .75 |
| 1 | 1 | .15 | .15 |

The first column of Table I lists varying initial percentage by volume of gas entrained in the fluid samples.

The second column of Table I indicates the percent error present in a non-pressurized fluid density measurement assuming that the density of the gas is insignificant compared to the density of the liquid portion of the fluid sample. Thus, it is seen that the percentage of error in the fluid density measurement is approximately equal to the percentage of entrained gas by volume present in the fluid sample.

The third column in Table I specifies the volume percent of entrained air or gas which is present in the same fluid samples of columns 1 and 2 after that fluid sample has been subjected to a pressure of 100 psig. It is seen that the percentage by volume of entrained air or gas is greatly reduced. The fourth column indicates the percentage error in a fluid density measurement under pressurized conditions. Again, the numbers in column 4 are the same as the numbers in column 3 since I have assumed that the density of the gas is significant compared to the density of the liquid.

Experience indicates that an average drilling mud sample will have on the order of 5% entrained air or gas by volume. A very bad sample might have 10%. If a greater amount of entrained air than 5 to 10 percent is present in the mud sample then usually foaming is occurring in the sample and a de-foaming agent should be added to the sample prior to conducting the fluid density measurement.

Thus, it is seen that for an average sample with an initial entrained air by volume of 5%, the error present in the fluid density measurement is decreased from 5% to 0.75% by the utilization of a pressurized density measuring apparatus such as that disclosed herein.

The downhole pressures within a well are typically on the order of thousands of psi but a pressure of 100 psi is sufficient to achieve most of the possible volume compression of entrained air since greater increases in pressure only add a very small additional volume compression of the entrained air. It has been determined that with the pump means 98 of the present invention the pressure provided thereby very easily exceeds 100 psi, and so the 100 psi assumption has been made on a very conservative basis for the figures given in Table I.

Thus, it is seen that the density measuring apparatus of the present invention readily achieves the ends and advantages mentioned as well as those inherent therein. While certain preferred embodiments of the present invention have been illustrated for the purpose of this disclosure, numerous changes in the arrangement and construction of parts may be made by those skilled in the art which changes are encompassed within the scope and spirit of this invention as defined by the appended claims

What is claimed is:

1. An apparatus for measuring density of a fluid in a pressurized state, comprising:

a balance arm;
a fulcrum means for supporting said balance arm;
a balance weight slidably disposed on said balance arm;
a pressurizable container means, disposed on said balance arm, for holding said fluid;
valve means, connected to said container means, for allowing pressurized fluid to flow into said container means and for retaining said fluid in said container means under pressure; and
pump means for supplying said pressurized fluid to said valve means, said pump means including:
a pump body having a cylindrical bore disposed therein and an outlet port means for communicating said bore with said valve means; and
a rotatable piston member means, threadedly engaged with said pump body, for pressurizing fluid contained in said bore upon rotation of said piston member means relative to said pump body, said pump body and said rotatable piston member means being so arranged and constructed that said fluid is maintained in a pressurized state when effort to rotate said rotatable piston member means is released.

2. The apparatus of claim 1, wherein:
said pump body is cylindrical and has a closed first end and an open second end;
said bore of said pump body includes a first bore portion adjacent said first end and an internally threaded second bore portion;
said outlet port means communicates with said first bore portion; and
said piston member means includes a first cylindrical portion closely received in said first bore portion of said pump body and a threaded second cylindrical portion engaged with said internally threaded second bore portion of said pump body.

3. The apparatus of claim 2, wherein:
said pump body is integrally constructed from a first single piece of plastic material; and
said piston member means is integrally constructed from a second single piece of plastic material.

4. The apparatus of claim 2, further comprising:
resilient seal means for sealing between said first cylindrical portion of said piston member means and said first bore portion of said pump body.

5. The apparatus of claim 4, wherein:
said first cylindrical portion of said piston member means has an annular groove disposed therein adjacent a first end of said piston member means; and
said resilient seal means includes a resilient O-ring disposed in said annular groove of said piston member means.

6. The apparatus of claim 2, wherein:
said first and second bore portions of said bore of said pump body are of substantially equal lengths.

7. The apparatus of claim 2, wherein:
said piston member means further includes a substantially disc shaped handgrip having an outer diameter greater than an outer diameter of said pump body.

8. The apparatus of claim 1, further comprising:
coupler means, connected to said pump means and detachably connected to said valve means, for permitting said pump means to be rapidly detached from said valve means.

9. The apparatus of claim 1, wherein:
said container means includes:
a cup having a closed bottom end and an open top end; and
a cap sealingly connected to said top end of said cup for covering said open top end, said cap having a valve bore disposed therethrough; and
said valve means includes a valve member threadedly engaged with an internally threaded part of said valve bore of said cap, said valve member having a fluid passage means disposed therethrough for selectively communicating said pump means with an interior of said cup, said valve member being movable, upon rotation thereof relative to said cap, between an open position wherein said fluid passage means is communicated with said interior of said cup and a closed position wherein said fluid passage means is isolated from said interior of said cup.

10. The apparatus of claim 1, wherein:
said pressurizable container means is detachable from said balance arm so that said container means may be connected to said pump means and pressurized while said container means is detached from said balance arm.

11. The apparatus of claim 10, wherein:
said balance arm has an outer cup attached thereto for receiving and holding said pressurizable container means.

12. The apparatus of claim 11, further comprising:
a weight means for lowering a center of gravity of said container means and said outer cup when said container means is received in said outer cup and said container means is filled with said fluid, so that when said balance arm is oriented horizontally, said center of gravity is below a horizontal line through a point of said fulcrum means upon which said balance arm rests.

13. An apparatus for measuring density of a fluid in either a pressurized or a non-pressurized state, comprising:
a balance arm;
a fulcrum means for supporting said balance arm;
a balance weight slidably disposed on said balance arm;
a first non-pressurized container means having a fixed volume for holding said fluid to measure the density thereof in a non-pressurized state, said first container means being attached to an end of said balance arm; and
a removable pressurizable second container means, received in said first container means, for holding said fluid to measure the density thereof in a pressurized state, said second container means having a fixed volume equal to said fixed volume of said first container means.

14. The apparatus of claim 13, further comprising:
counterbalance means, connectable to said balance arm, for counterbalancing a weight of said second container means when measuring the density of said fluid in a pressurized state.

15. The apparatus of claim 13, further comprising:
valve means, connected to said second container means, for allowing pressurized fluid to flow into said second container means and for retaining said fluid in said second container means under pressure; and
pump means, detachably connected to said valve means, for supplying said pressurized fluid to said valve means.

16. The apparatus of claim 15, further comprising:
coupler means, connected to said pump means and detachably connected to said valve means, for permitting said pump means to be rapidly detached from said valve means.

17. The apparatus of claim 13, further comprising:
a weight means for lowering a center of gravity of said first and second container means when said second container means is received in said first container means and said second container means is filled with said fluid, so that when said balance arm is oriented horizontally, said center of gravity is below a horizontal line through a point of said fulcrum means upon which said balance arm rests.

18. An apparatus for measuring density of a fluid in a pressurized state, comprising:
a pressurizable container means for holding said fluid, said container means having a valve bore disposed therethrough;
a pump means for supplying pressurized fluid to said container means; and
a valve member threadedly engaged with an internally threaded part of said valve bore, said valve member having a fluid passage means disposed therethrough for selectively communicating said pump means with an interior of said container means, said valve member being movable, upon rotation thereof relative to said container means, between an open position wherein said fluid passage means is communicated with said interior of said container means and a closed position wherein said fluid passage means is isolated from said interior of said container means.

19. The apparatus of claim 18, wherein:
said valve bore of said container means includes:
a smaller diameter bore portion communicated with said interior of said container means;
a larger diameter bore portion located above said smaller diameter bore portion; and
a downwardly tapered annular inner surface connecting said larger and smaller bore portions; and
said valve member includes:
a smaller outer diameter portion closely received in said smaller diameter bore portion of said container means when said valve member is in its said closed position;
a larger outer diameter portion closely received in said larger diameter bore portion of said container means;
a downwardly tapered annular outer surface connecting said larger and smaller outer diameter portions, said fluid passage means having a lower end communicated with said downwardly tapered annular outer surface;
upper resilient annular sealing means for sealing between said larger outer diameter portion of said valve member and said larger diameter bore portion of said valve bore of said container means; and
lower resilient annular sealing means for sealing between said smaller outer diameter portion of said valve member and said smaller diameter bore portion of said valve bore of said container means when said valve member is in its closed position.

20. The apparatus of claim 18 wherein:
said valve member includes a radially outward extending flange at an upper end thereof with an upper end of said fluid passage means communicating with an upper surface of said flange; and
said apparatus further comprises a coupler means connected to said pump means and including a recess means for closely receiving said flange of said valve member upon insertion of said flange into said recess means in a direction parallel to a plane of said flange so that said pump means is communicated with said fluid passage means when said flange is received in said recess means of said coupler means.

21. The apparatus of claim 20, wherein:
said coupler means further includes annular resilient seal means disposed about said upper end of said fluid passage means of said valve member when said flange is received in said recess means.

22. The apparatus of claim 18 wherein:
said pump means includes a pump body having a cylindrical bore disposed therein, and a rotatable piston member means threadedly engaged with said pump body for pressurizing fluid contained in said bore upon rotation of said piston member means relative to said pump body.

23. An apparatus for measuring density of a fluid in a pressurized state, comprising:
a container means for holding said fluid;
a cover means, connected to said container means and including a piston member closely received within said container means so that said container means and said piston member define a closed pressurizing chamber, said piston member being longitudinally movable to an inwardmost position relative to said container means at which inwardmost position said pressurizing chamber has a fixed volume; and
a pressure regulating means, communicated with said pressurizing chamber, for relieving fluid pressure in said pressurizing chamber in excess of a predetermined pressure.

24. The apparatus of claim 23, wherein:
said cover means is threadedly engaged with said container means; and
said piston member is longitudinally movable relative to said container means upon rotation of said cover means relative to said container means.

25. The apparatus of claim 24, further comprising:
resilient seal means for sealing between said piston member and said container means.

26. The apparatus of claim 23, further comprising:
a balance arm, said container means being disposed on said balance arm;
a fulcrum means for supporting said balance arm; and
a balance weight slidably disposed on said balance arm.

27. An apparatus for measuring density of a fluid in a pressurized state, comprising:
a balance arm;
a fulcrum means for supporting said balance arm;
a balance weight slidably disposed on said balance arm;
a pressurizable container means, disposed on said balance arm, for holding said fluid;
valve means, connected to said container means, for allowing pressurized fluid to flow into said container means and for retaining said fluid in said container means under pressure;

pump means for supplying said pressurized fluid to said valve means, said pump means including:
  a pump body having a cylindrical bore disposed therein and an outlet port means for communicating said bore with said valve means; and
  a rotatable piston member means, threadedly engaged with said pump body, for pressurizing fluid contained in said bore upon rotation of said piston member means relative to said pump body;
wherein said container means includes:
a cup having a closed bottom end and an open top end; and
  a cap sealingly connected to said top end of said cup for covering said open top end, said cap having a valve bore disposed therethrough;
wherein said valve means includes a valve member threadedly engaged with an internally threaded part of said valve bore of said cap, said valve member having a fluid passage means disposed therethrough for selectively communicating said pump means with an interior of said cup, said valve member being movable, upon rotation thereof relative to said cap, between an open position wherein said fluid passage means is communicated with said interior of said cup and a closed position wherein said fluid passage means is isolated from said interior of said cup;
wherein said valve bore of said cap includes:
  a smaller diameter bore portion located communicated with said interior of said cup;
  a larger diameter bore portion above said smaller diameter bore portion; and
  a downwardly tapered annular inner surface connecting said larger and smaller bore portions; and
wherein said valve member includes:
  a smaller outer diameter portion closely received in said smaller diameter bore portion of said cap when said valve member is in its said closed position;
  a larger outer diameter portion closely received in said larger diameter bore portion of said cap;
  a downwardly tapered annular outer surface connecting said larger and smaller outer diameter portions, said fluid passage means having a lower end communicated with said downwardly tapered annular outer surface;
  upper resilient annular sealing means for sealing between said larger outer diameter portion of said valve member and said larger diameter bore portion of said valve bore of said cap; and
  lower resilient annular sealing means for sealing between said smaller outer diameter portion of said valve member and said smaller diameter bore portion of said valve bore of said cap when said valve member is in its closed position.

28. An apparatus for measuring density of a fluid in a pressurized state, comprising:
  a balance arm;
  a fulcrum means for supporting said balance arm;
  a balance weight slidably disposed on said balance arm;
  a pressurizable container means, disposed on said balance arm, for holding said fluid;
  valve means, connected to said container means, for allowing pressurized fluid to flow into said container means and for retaining said fluid in said container means under pressure;
  pump means for supplying said pressurized fluid to said valve means, said pump means including:
    a pump body having a cylindrical bore disposed therein and an outlet port means for communicating said bore with said valve means; and
    a rotatable piston member means, threadedly engaged with said pump body, for pressurizing fluid contained in said bore upon rotation of said piston member means relative to said pump body;
  wherein said container means includes:
    a cup having a closed bottom end and an open top end; and
    a cap sealingly connected to said top end of said cup for covering said open top end, said cap having a valve bore disposed therethrough;
  wherein said valve means includes a valve member threadedly engaged with an internally threaded part of said valve bore of said cap, said valve member having a fluid passage means disposed therethrough for selectively communicating said pump means with an interior of said cup, said valve member being movable, upon rotation thereof relative to said cap, between an open position wherein said fluid passage means is communicated with said interior of said cup and a closed position wherein said fluid passage means is isolated from said interior of said cup;
  wherein said valve member includes a radially outward extending flange at an upper end thereof with an upper end of said fluid passage means communicating with an upper surface of said flange; and
  wherein said apparatus further comprises a coupler means connected to said pump means and including a recess means for closely receiving said flange of said valve member upon insertion of said flange into said recess means in a direction parallel to a plane of said flange so that said pump means is communicated with said fluid passage means when said flange is received in said recess means of said coupler means.

29. The apparatus of claim 28, wherein:
  said coupler means further includes annular resilient seal means disposed about said upper end of said fluid passage means of said valve member when said flange is received in said recess means.

* * * * *